United States Patent
Imamura et al.

(10) Patent No.: US 8,322,854 B2
(45) Date of Patent: Dec. 4, 2012

(54) EYE PORTION DIAGNOSIS SUPPORT APPARATUS, METHOD THEREFOR, PROGRAM, AND RECORDING MEDIUM

(75) Inventors: Hiroshi Imamura, Tokyo (JP); Akihiro Katayama, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/177,877

(22) Filed: Jul. 7, 2011

(65) Prior Publication Data

US 2011/0267584 A1 Nov. 3, 2011

Related U.S. Application Data

(63) Continuation of application No. 12/966,917, filed on Dec. 13, 2010, now Pat. No. 7,980,695, which is a continuation of application No. 12/769,401, filed on Apr. 28, 2010, now Pat. No. 7,857,449, which is a continuation of application No. PCT/JP2009/002281, filed on May 25, 2009.

(30) Foreign Application Priority Data

Jul. 31, 2008 (JP) ................................. 2008-198623

(51) Int. Cl.
 *A61B 3/14* (2006.01)
(52) U.S. Cl. ........................................ 351/206; 351/246
(58) Field of Classification Search .................. 351/205, 351/206, 210, 246
See application file for complete search history.

(56) References Cited

U.S. PATENT DOCUMENTS

| | | |
|---|---|---|
| 6,293,674 B1 | 9/2001 | Huang et al. |
| 7,474,775 B2 * | 1/2009 | Abramoff et al. ............. 382/128 |

FOREIGN PATENT DOCUMENTS

| | | | |
|---|---|---|---|
| JP | 2004-502483 A | 1/2004 | |
| JP | 2007-117714 | * 5/2007 | ................... 351/206 |
| JP | 2007-130403 A | 5/2007 | |
| JP | 2007-275374 A | 10/2007 | |
| JP | 2008-154704 A | 7/2008 | |
| JP | 2008-289579 A | 12/2008 | |
| WO | WO2006/022045 A | 3/2006 | |
| WO | WO2007/084748 A | 7/2007 | |

* cited by examiner

*Primary Examiner* — Huy K Mai
(74) *Attorney, Agent, or Firm* — Canon U.S.A., Inc., IP Division

(57) ABSTRACT

There is provided a technique for efficiently acquiring a tomogram of an eye portion. A diagnosis support apparatus includes a wide-area image acquisition means for acquiring a wide-area image of an eye portion, a detection means for detecting a lesion candidate on the eye portion by analyzing the wide-area image acquired by the wide-area image acquisition means, a determination means for determining a parameter associated with acquisition of a tomogram of the eye portion, based on a lesion candidate detection result obtained by the detection means, and a tomogram acquisition means for acquiring a tomogram of the eye portion based on the parameter determined by the determination means.

12 Claims, 6 Drawing Sheets

ER PORTION DIAGNOSIS SUPPORT APPARATUS, METHOD THEREFOR, PROGRAM, AND RECORDING MEDIUM

CROSS REFERENCE TO RELATED APPLICATIONS

This application is a Continuation of U.S. patent application Ser. No. 12/966,917, filed Dec. 13, 2010, which is a Continuation of U.S. patent application Ser. No. 12/769,401, filed Apr. 28, 2010, now issued as U.S. Pat. No. 7,857,449, which is a continuation of PCT Application No. PCT/JP2009/002281, filed May 25, 2009, which claims priority to Japanese Patent Application No. 2008-198623 filed Jul. 31, 2008, each of which are hereby incorporated by reference in their entireties.

TECHNICAL FIELD

The present invention relates to a diagnosis support apparatus, a method therefor, a program, and a recording medium and, more particularly, to a technique for efficiently performing image diagnosis of an eye portion.

BACKGROUND ART

Examination on eye portions is widely practiced for the purpose of early diagnosis of life-style related diseases and various kinds of diseases ranking high in causes of blindness. In a health check or the like, it is required to find a disease in an entire eye portion, and hence an examination using an image covering a wide range of an eye portion (to be referred to as a wide-area image hereinafter) is indispensable. A wide-area image is obtained by using, for example, a fundus camera or SLO (Scanning Laser Ophthalmoscope).

On the other hand, a tomogram acquisition apparatus for eye portions such as an OCT (Optical Coherence Tomography) apparatus can quantify the state of a disease with an objective measure, and hence is expected to be useful in more accurate examination of a disease. When using a general OCT, the operator determines tomographic imaging parameters (e.g., a target region, imaging range, resolution, and scanning method), and only a local region of an eye portion is imaged/analyzed based on the imaging parameters.

As a technique of supporting tomographic imaging performed by an operator, for example, patent reference 1 discloses a technique associated with a user interface for designating a tomographic imaging range by an OCT on a wide-area image obtained by a fundus camera. In addition, patent reference 2 discloses a technique associated with a user interface for designating a tomographic imaging range by an OCT on a wide-area image obtained by an SLO. According to patent references 1 and 2, it is possible to determine a tomographic imaging range while referring to the state of a wide-area image of the fundus.

PRIOR ART REFERENCE

Patent References

Patent reference 1: Japanese Patent Laid-Open No. 2007-117714
Patent reference 2: Japanese Patent Laid-Open No. 2008-029467

DISCLOSURE OF INVENTION

Problems that the Invention is to Solve

Assume that an operator manually designates imaging parameters to obtain tomograms. In this case, if the operator is not an ophthalmologist, in particular, the operator cannot necessarily set proper imaging parameters including an imaging region. In some cases, therefore, it is not possible to obtain any tomogram required for diagnosis. Assume also that the arrangements disclosed in patent references 1 and 2 are used. Even in this case, since the position of a lesion which can be grasped on a wide-area image does not necessarily coincide with a region whose tomogram should be obtained, it is not always easy to set imaging parameters.

Assume also that a tomogram covering a wide range has been obtained by some kind of method. Even in this case, if a diagnostician is not an ophthalmologist, it is not easy for him/her to determine which part of the tomogram is to be analyzed/measured.

The present invention has been made in consideration of the above problem, and has as its object to provide a technique for efficiently acquiring a tomogram of an eye portion.

Means of Solving the Problems

In order to achieve the above object, a diagnosis support apparatus according to the present invention has the following arrangement. That is, the apparatus is characterized by comprising wide-area image acquisition means for acquiring a wide-area image of an eye portion, detection means for detecting a lesion candidate on the eye portion by analyzing the wide-area image acquired by the wide-area image acquisition means, determination means for determining a parameter associated with acquisition of a tomogram of the eye portion, based on a lesion candidate detection result obtained by the detection means, and tomogram acquisition means for acquiring a tomogram of the eye portion based on the parameter determined by the determination means.

In addition, another diagnosis support apparatus according to the present invention has the following arrangement. That is, the other apparatus is characterized by comprising wide-area image acquisition means for acquiring a wide-area image of an eye portion, detection means for detecting a lesion candidate on the eye portion by analyzing the wide-area image acquired by the wide-area image acquisition means, determination means for determining a parameter associated with acquisition of a tomogram of the eye portion, based on a lesion candidate detection result obtained by the detection means, and saving means for saving the parameter determined by the determination means in storage means in association with the wide-area image acquired by the wide-area image acquisition means.

A diagnosis support method for a diagnosis support apparatus according to the present invention has the following arrangement. That is, the method is characterized by comprising the wide-area image acquisition step of acquiring a wide-area image of an eye portion, the detection step of detecting a lesion candidate on the eye portion by analyzing the wide-area image acquired in the wide-area image acquisition step, the determination step of determining a parameter associated with acquisition of a tomogram of the eye portion, based on a lesion candidate detection result obtained in the detection step, and the tomogram acquisition step of acquiring a tomogram of the eye portion based on the parameter determined in determination step.

In addition, another diagnosis support method for a diagnosis support apparatus according to the present invention has the following arrangement. That is, the other method is characterized by comprising the wide-area image acquisition step of acquiring a wide-area image of an eye portion, the detection step of detecting a lesion candidate on an eye portion by analyzing the wide-area image acquired in the wide-area image acquisition step, the determination step of determining a parameter associated with acquisition of a tomogram of the eye portion, based on a lesion candidate detection result obtained in the detection step, and the saving step of saving the parameter determined in the determination step in storage means in association with the wide-area image acquired in the wide-area image acquisition step.

Effect of the Invention

According to the present invention, a technique for efficiently acquiring a tomogram of an eye portion can be provided.

Other features and advantages of the present invention will be apparent from the following description taken in conjunction with the accompanying drawings, in which like reference numerals designate the same or similar parts throughout the figures thereof.

BRIEF DESCRIPTION OF DRAWINGS

The accompanying drawings, which are incorporated in and constitute a part of the specification, illustrate embodiments of the invention and, together with the description, serve to explain the principles of the invention.

BEST MODE FOR CARRYING OUT THE INVENTION

The embodiments of the present invention will be described in detail below with reference to the accompanying drawings. Note however that the constituent elements described in the embodiments are merely examples, and the scope of the present invention is not limited to them. In addition, not all combinations of the features described in the embodiments are necessarily essential to the means of solving provided by the present invention.

First Embodiment

Arrangement for Acquiring Wide-Area Image/Tomogram from Imaging Device (Device Configuration of Diagnosis Support Apparatus)

Figure 1:
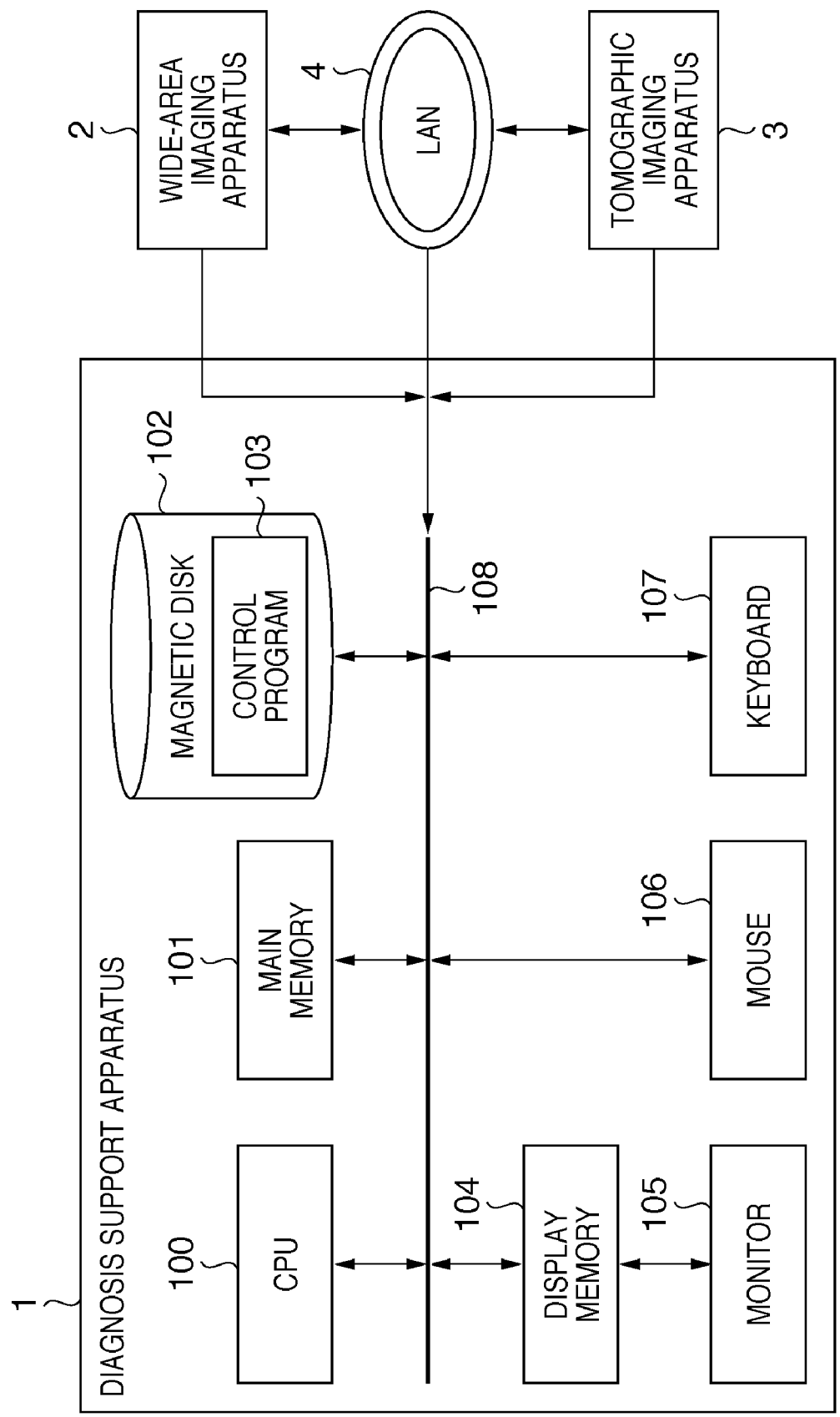
FIG. 1 is a block diagram showing an example of the device configuration of a diagnosis support apparatus.

The device configuration of a diagnosis support apparatus 1 according to this embodiment will be described first. FIG. 1 is a block diagram showing the device configuration of the diagnosis support apparatus 1 according to the embodiment. The diagnosis support apparatus 1 in FIG. 1 includes a central processing unit (CPU) 100, a main memory 101, a magnetic disk 102, control programs 103, a display memory 104, a monitor 105, a mouse 106, a keyboard 107, and a common bus 108.

The central processing unit (CPU) 100 mainly controls the operation of each constituent element of the diagnosis support apparatus 1. The main memory 101 can be implemented by a RAM (Random Access Memory). The main memory 101 stores apparatus control programs and serves as a work area at the time of execution of a program. The magnetic disk 102 stores an operating system (OS), device drivers for peripheral devices, the programs 103 for executing various kinds of processes (to be described later), and the like.

The display memory 104 temporarily stores display data. The monitor 105 is, for example, a CRT monitor or a liquid crystal monitor. The monitor 105 displays an image based on data from the display memory 104. The mouse 106 and the keyboard 107 are operated by a user to perform pointing input operation and input characters and the like. The respective constituent elements described above are connected to each other via the common bus 108.

As shown in FIG. 1, the diagnosis support apparatus 1 is connected to a wide-area imaging apparatus 2 and a tomographic imaging apparatus (tomogram acquisition apparatus) 3 via a local area network (LAN) 4 by Ethernet® or the like. Note that these devices may be connected to each other via an external interface such as USB or IEEE1394.

Figure 4:
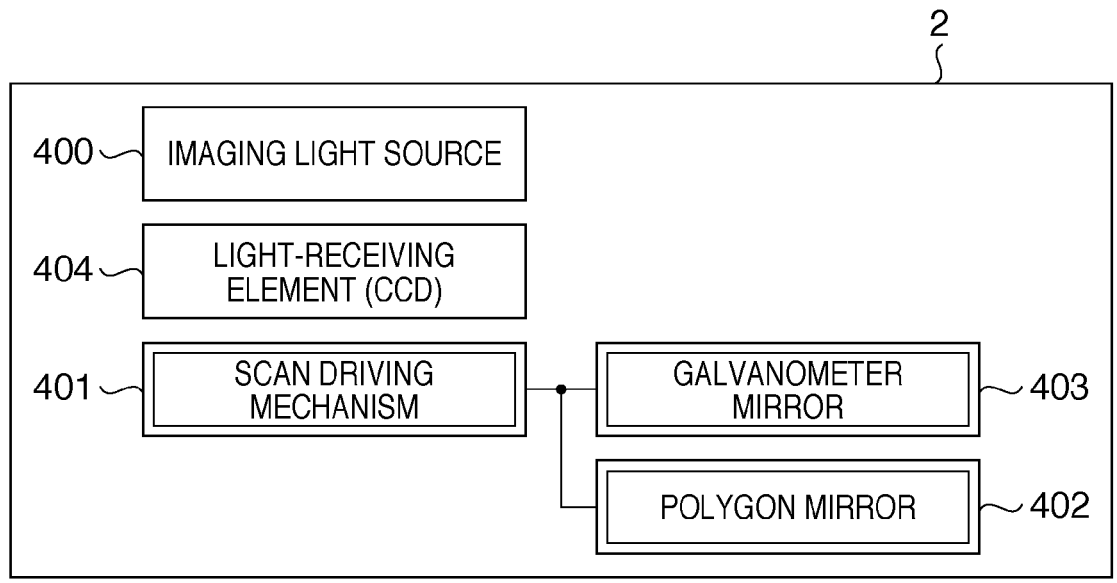
FIG. 4 is a block diagram showing an example of the arrangement of a wide-area imaging apparatus.

The wide-area imaging apparatus 2 is an apparatus to obtain a wide-area image of an eye portion, and can be implemented by, for example, a fundus camera or an SLO. FIG. 4 is a block diagram showing the arrangement of the wide-area imaging apparatus 2 implemented by an SLO (Scanning Laser Ophthalmoscope).

The wide-area imaging apparatus 2 obtains a wide-area image of an eye portion in accordance with a request from the diagnosis support apparatus 1, and outputs the obtained wide-area image to the diagnosis support apparatus 1. As shown in FIG. 4, the wide-area imaging apparatus 2 controls a polygon mirror 402 and a galvanometer mirror 403 through a scan driving mechanism 401 to obtain a wide-area image of an eye portion. The wide-area imaging apparatus 2 then obtains a wide-area image of an eye portion by receiving reflected light of weak laser light emitted from an imaging light source 400 via a light-receiving element 404. Note that the device configuration of the SLO and driving mechanism control are described in detail in patent reference 2.

Figure 6:
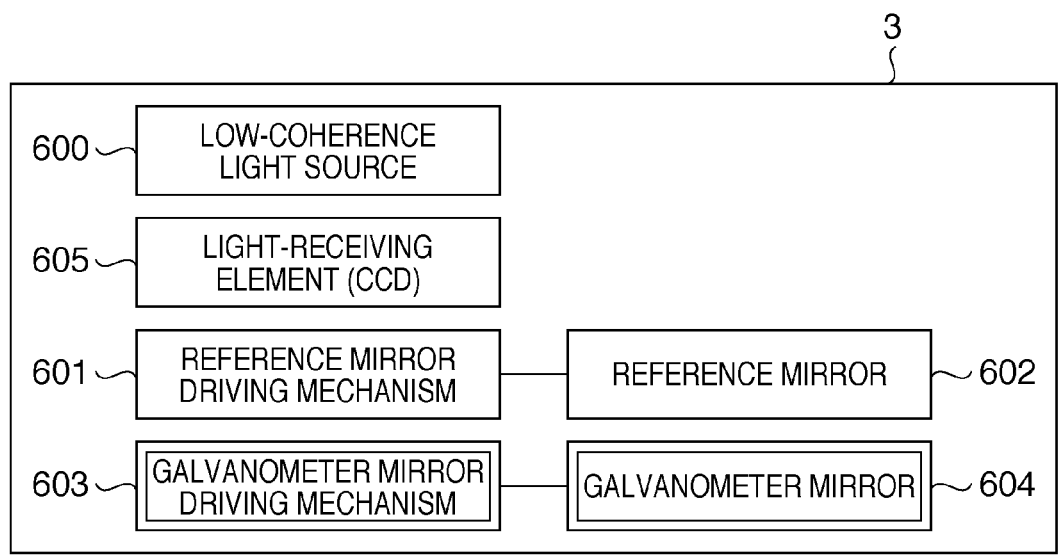
FIG. 6 is a block diagram showing an example of the arrangement of a tomographic imaging apparatus.

The tomographic imaging apparatus 3 is an apparatus to obtain a tomogram of an eye portion, and includes, for example, a time-domain OCT (TD-OCT) or a Fourier domain OCT (FD-OCT). FIG. 6 is a block diagram showing an example of the arrangement of the tomographic imaging apparatus 3 in a case in which the tomographic imaging apparatus 3 is a time-domain OCT. The tomographic imaging apparatus 3 receives parameters designating the contents of imaging from the diagnosis support apparatus 1, and obtains a tomogram by using the parameters. The tomographic imaging apparatus 3 outputs the obtained tomogram to the diagnosis support apparatus 1.

The parameters designating the contents of imaging in this case are parameters designating a tomogram acquisition region, the spatial range of the tomogram, a resolution such as a scanning line interval, and a scanning method including a scanning order and a scanning direction. The tomographic imaging apparatus 3 controls a reference mirror driving mechanism 601 and a galvanometer mirror driving mechanism 603 in accordance with these parameters to drive a reference mirror 602 and a galvanometer mirror 604. The tomographic imaging apparatus 3 then obtains a tomogram of an eye portion by receiving, via a light-receiving element 605, reflected light of light emitted by a low-coherence light source 600. Note that if the tomographic imaging apparatus 3 is a Fourier domain OCT, only the galvanometer mirror 604 is controlled. The device configurations of these OCTs and driving mechanism control are described in detail in patent references 1 and 2.

(Functional Arrangement of Diagnosis Support Apparatus)

Figure 2:
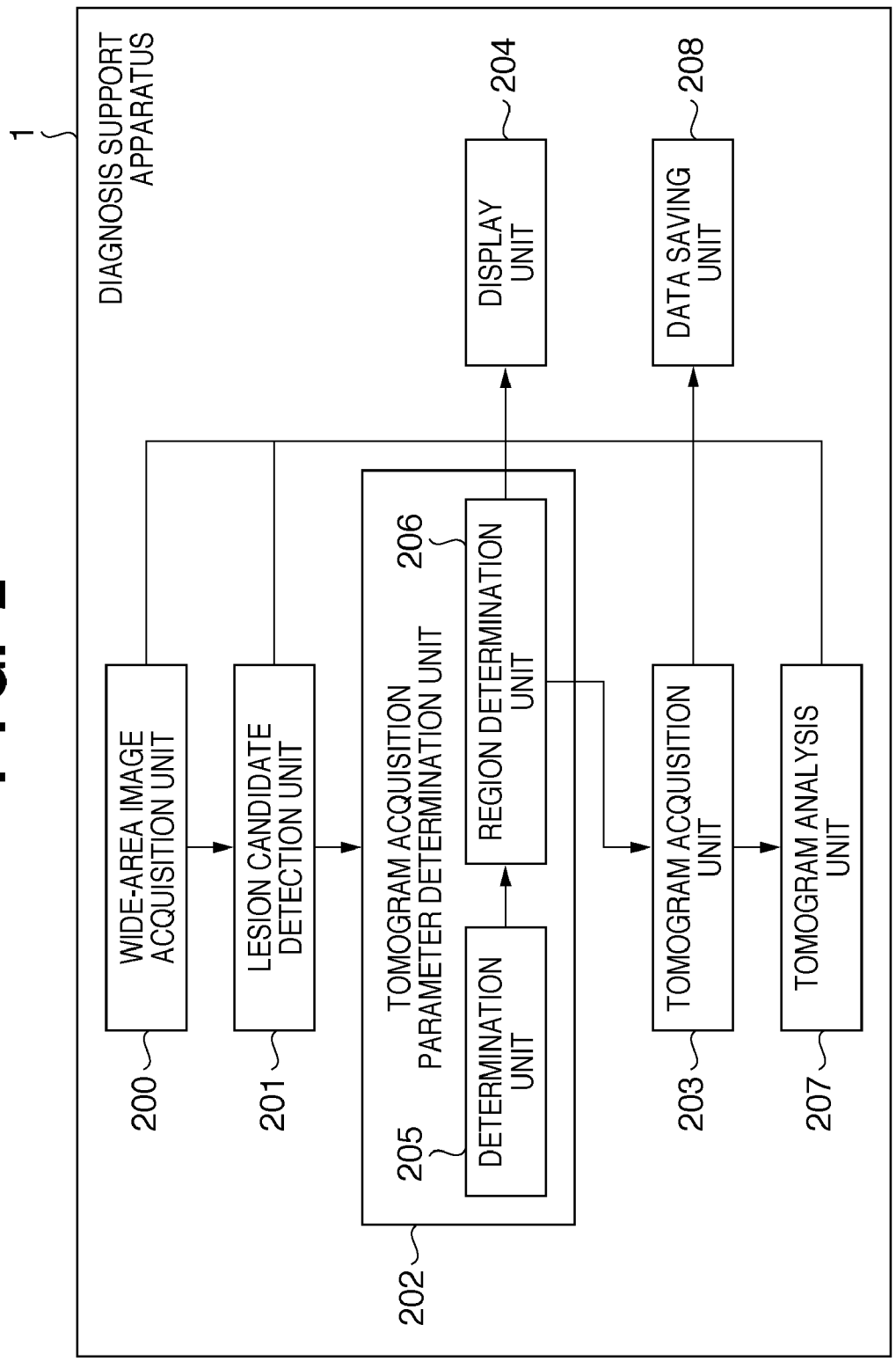
FIG. 2 is a functional block diagram showing an example of the functional arrangement of the diagnosis support apparatus.

The functional arrangement of the diagnosis support apparatus 1 will be described next with reference to FIG. 2. FIG. 2 is a functional block diagram showing the functional arrangement of the diagnosis support apparatus 1 in this embodiment. As shown in FIG. 2, the diagnosis support apparatus 1 includes a wide-area image acquisition unit 200, a lesion candidate detection unit 201, a tomogram acquisition parameter determination unit 202, a tomogram acquisition unit 203, a display unit 204, and a data saving unit 208.

Wide-Area Image Acquisition Unit 200

The wide-area image acquisition unit 200 requests the wide-area imaging apparatus 2 to obtain and transmit a wide-area image of an eye portion, and acquires the wide-area image of the eye portion transmitted from the wide-area imaging apparatus 2. The wide-area image acquired by the wide-area image acquisition unit 200 is transmitted to the lesion candidate detection unit 201, the display unit 204, and the data saving unit 208.

Lesion Candidate Detection Unit 201

The lesion candidate detection unit 201 detects information associated with lesion candidates from the wide-area image of the eye portion acquired by the wide-area image acquisition unit 200 based on information from a normal eye database, a medical care guideline, and the like. The information associated with the lesion candidate detected by the lesion candidate detection unit 201 (lesion candidate detection result) is transmitted to the tomogram acquisition parameter determination unit 202, display unit 204, and data saving unit 208. The contents of a specific process for detecting lesion candidates from a wide-area image will be described in detail later.

Tomogram Acquisition Parameter Determination Unit 202

The tomogram acquisition parameter determination unit 202 includes a determination unit 205 and a region determination unit 206. The tomogram acquisition parameter determination unit 202 determines parameters associated with the acquisition of a tomogram (tomographic imaging parameters) based on information associated with the lesion candidate detected by the lesion candidate detection unit 201 (lesion candidate detection result). The tomographic imaging parameters include a parameter designating necessity/unnecessity of the acquisition of a tomogram and parameters designating the contents of imaging. The determination unit 205 determines the former, and the region determination unit 206 determines the latter. The imaging parameters determined by the tomogram acquisition parameter determination unit 202 are transmitted to the tomogram acquisition unit 203, a tomogram analysis unit 207, the display unit 204, and the data saving unit 208. The contents of a specific process for determining tomographic imaging parameters based on a lesion candidate detection result will be described in detail later.

Tomogram Acquisition Unit 203

If the parameter designating the necessity/unnecessity of the acquisition of a tomogram determined by the tomogram acquisition parameter determination unit 202 indicates necessity, the tomogram acquisition unit 203 transmits a tomographic imaging request to the tomographic imaging apparatus 3, together with parameters designating the contents of imaging. The tomogram acquisition unit 203 then acquires the tomogram transmitted from the tomographic imaging apparatus 3. The tomogram acquired by the tomogram acquisition unit 203 is transmitted to the tomogram analysis unit 207, display unit 204, and data saving unit 208.

Tomogram Analysis Unit 207

The tomogram analysis unit 207 analyzes the tomogram acquired by the tomogram acquisition unit 203, and performs image measurement associated with the tomogram or lesion candidate detection from the tomogram. The analysis result is then transmitted to the display unit 204 and the data saving unit 208. Note that the contents of a concrete process for analyzing a tomogram will be described in detail later.

Display Unit 204

The display unit 204 displays the tomogram obtained by the tomogram acquisition unit 203 and the image measurement or lesion candidate detection result obtained by the tomogram analysis unit 207. In addition, the display unit 204 displays the tomographic imaging parameters determined by the tomogram acquisition parameter determination unit 202. If no tomogram can be acquired, the display unit 204 displays information indicating it. Furthermore, for the purpose of checking an imaging region, the display unit 204 may also display altogether the wide-area image acquired by the wide-area image acquisition unit 200 and the information associated with the lesion candidates detected by the lesion candidate detection unit 201.

Data Saving Unit 208

The data saving unit 208 saves various kinds of input information in association with each other as data of a given patient in the magnetic disk 102. More specifically, the data saving unit 208 saves the following information:

the wide-area image input from the wide-area image acquisition unit 200;

the information associated with the lesion candidates input from the lesion candidate detection unit 201;

the tomographic imaging parameters input from the tomogram acquisition parameter determination unit 202;

the tomogram input from the tomogram acquisition unit 203; and the image measurement or lesion candidate detection result input from the tomogram analysis unit 207. An external server (not shown) may save the data. In this case, the data saving unit 208 transmits these data to the external server.

(Diagnosis Support Processing)

Figure 3:
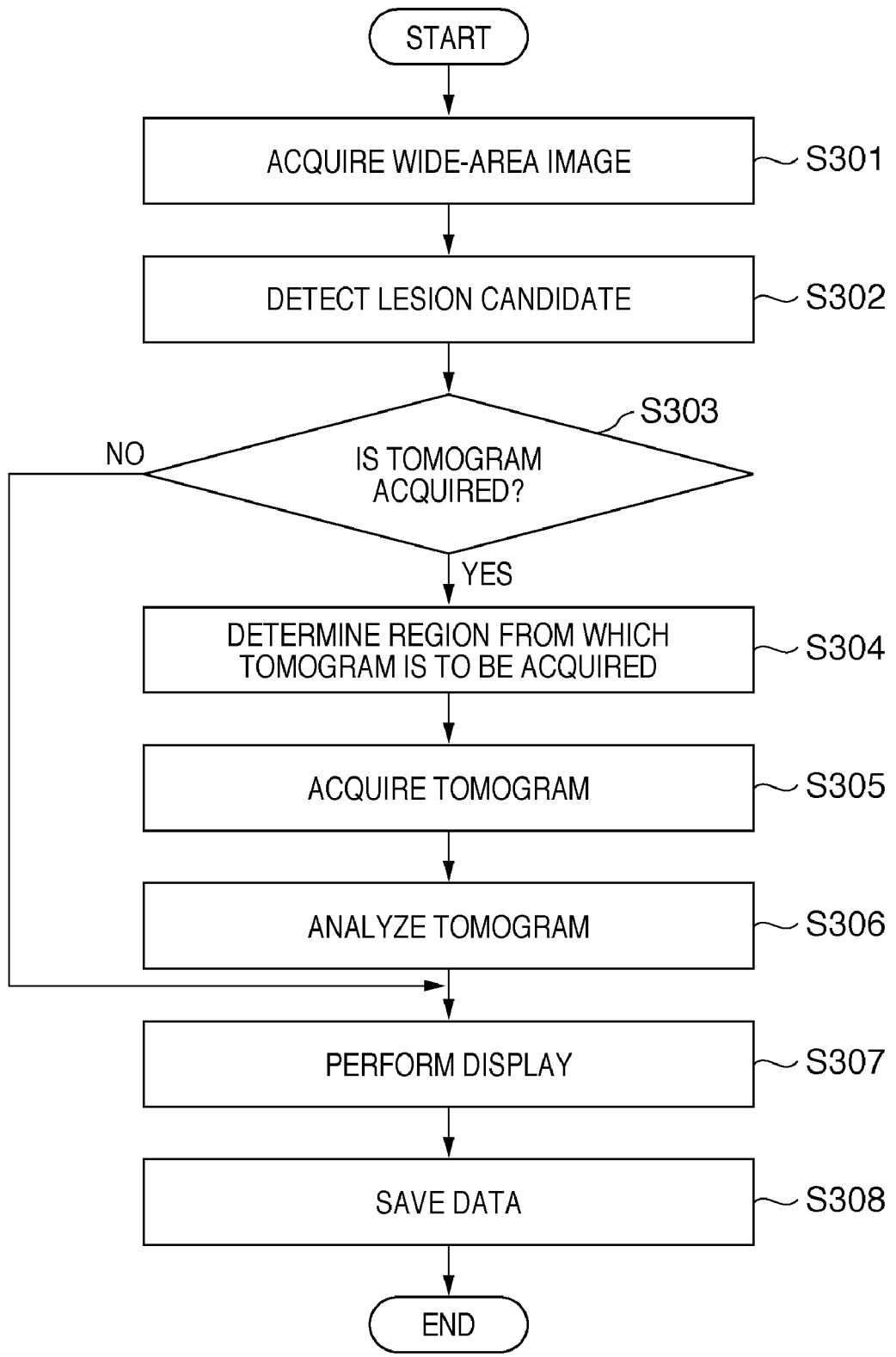
FIG. 3 is a flowchart showing a processing sequence for diagnosis support processing executed by the diagnosis support apparatus.

A concrete processing sequence for diagnosis support processing executed by the diagnosis support apparatus 1 of this embodiment will be described next with reference to FIG. 3. FIG. 3 is a flowchart showing a processing sequence for diagnosis support processing executed by the diagnosis support apparatus 1 according to this embodiment.

Step S301

In step S301, the wide-area image acquisition unit 200 requests the wide-area imaging apparatus 2 to obtain and transmit a wide-area image of an eye portion, and acquires the wide-area image of the eye portion transmitted from the wide-area imaging apparatus 2. The wide-area image acquisition unit 200 transmits the acquired wide-area image to the lesion candidate detection unit 201, display unit 204, and data saving unit 208.

Step S302

Figure 5:
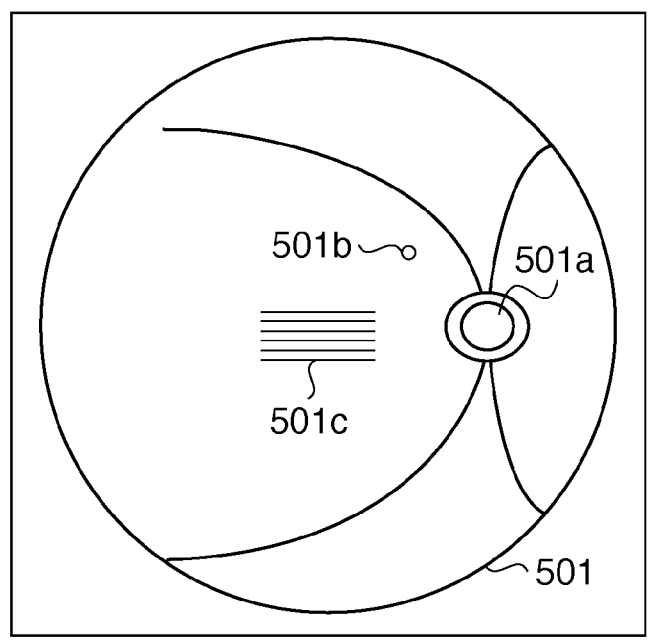
FIG. 5 is a view showing an example of lesion candidates on a wide-area image of an eye portion.

In step S302, the lesion candidate detection unit 201 detects information associated with lesion candidates by performing image processing (analysis) for the wide-area image acquired in step S301. The lesion candidate detection unit 201 in this embodiment detects, as lesion candidates, the geometric abnormality of an optic papilla 501a indicated by a schematic view 501 in FIG. 5, a nerve fiber layer deficit (not shown), the geometric abnormality of a blood vessel (not shown) such as arteriovenous crossing, and other lesion candidates such as a soft drusen 501b. The information associated with the detected lesion candidate (lesion candidate detection result) is transmitted to the tomogram acquisition parameter determination unit 202, display unit 204, and data saving unit 208. FIG. 5 is a view showing an example of the lesion candidates on the wide-area image of the eye portion detected by the lesion candidate detection unit 201.

Note that information associated with a lesion candidate includes information associated with the presence/absence of the lesion candidate, the type of lesion candidate, the range of the lesion candidate, and the degree of the lesion candidate. For example, information associated with the geometric abnormality of the optic papilla represents the presence/absence of geometric abnormality and a malignancy (a cup/disc ratio). Information associated with a nerve fiber layer deficit represents the presence/absence of a deficit and its existing range (coordinates/area). Information associated with the geometric abnormality of a blood vessel represents the presence/absence and coordinates of a lesion candidate and a malignancy (a vein diameter ratio). In addition, information associated with other lesions such as the soft drusen 501b represents the presence/absence of a lesion candidate, the coordinates and area of each lesion, and the number of lesions.

In this case, it is possible to detect the geometric abnormality of the optic papilla and a nerve fiber layer deficit by using, for example, the technique disclosed in patent reference 3. In addition, it is possible to detect the geometric abnormality of a blood vessel such as an arteriovenous crossing phenomenon by using, for example, the technique disclosed in non-patent reference 1. Furthermore, it is possible to detect other lesion candidates such as a soft drusen by using, for example, the technique disclosed in non-patent reference 2. Note that detection methods to be used for the respective lesion candidates are not limited to those described above, and any methods can be used as long as they can detect the respective lesion candidates from a wide-area image of an eye portion.
Patent reference 3: Japanese Patent Laid-Open No. 9-313447
Non-patent reference 1: Ryo Takahashi et al., "Automated Analysis of Blood Vessel Intersections in Retinal Images for Diagnosis of Hypertension", Medical Imaging Technology, Vol. 24, No. 4, pp. 270-276, 2006
Non-patent reference 2: Takuro Iwasaki et al., "An automatic extraction procedure of Drusen region in the fundus image", IEIC Technical Report, MI2003-100, pp. 17-22, 2004

Step S303

In step S303, the determination unit 205 determines the necessity/unnecessity of the acquisition of a tomogram based on the information associated with the lesion candidate detected in step S302 (lesion candidate detection result). The determination unit 205 then sets the result as a parameter designating the necessity/unnecessity of the acquisition of a tomogram, and transmits it to the tomogram acquisition unit 203, display unit 204, and data saving unit 208. If the determination unit 205 determines that it is necessary to acquire a tomogram (YES in step S303), the process advances to step S304. If the determination unit 205 determines that it is unnecessary to acquire a tomogram (NO in step S303), the process advances to step S307.

Based on information such as a medical care guideline, the determination unit 205 determines the necessity/unnecessity of the acquisition of a tomogram from the seriousness or occurrence region of a lesion candidate which is set in advance. More specifically, in the case of the geometric abnormality of an optic papilla, if the cup/disc ratio is equal to or more than a predetermined value (e.g., 0.7), it is determined that the acquisition of a tomogram is necessary. In the case of a nerve fiber layer deficit, if there is a deficit candidate region having an area equal to or more than a predetermined value, it is determined that the acquisition of a tomogram is necessary. In the case of an arteriovenous crossing phenomenon, if (the vein diameter at the crossing)/(the vein diameter at a portion other than the crossing) is a predetermined value (less than 1.0), it is determined that the acquisition of a tomogram is necessary. In the case of other lesions such as a soft drusen, if there is one or more lesion candidates having areas equal to or more than a predetermined value, it is determined that the acquisition of a tomogram is necessary.

Note that the method to be used to determine the necessity/unnecessity of the acquisition of a tomogram is not limited to this, and determination can be made based on other criteria. For example, if the lesion candidate detection unit 201 detects some kind of lesion candidate, it can be determined that the acquisition is necessary, and vice versa.

Step S304

In step S304, the region determination unit 206 determines parameters designating the contents of tomography based on information associated with the lesion candidate detected in step S302 (lesion candidate detection result). The region determination unit 206 then transmits the determined parameters to the tomogram acquisition unit 203, tomogram analysis unit 207, display unit 204, and data saving unit 208.

The region determination unit 206 determines parameters designating the contents of tomography in accordance with the type and state (position and range) of the detected lesion candidate. More specifically, the region determination unit 206 determines the spatial range of a tomogram, a resolution such as a scanning line interval, and a scanning method including a scanning order and a scanning direction, which are suitable for the type of lesion and a tomogram acquisition region. The following are a concrete example of parameters that can be set.

When Geometric Abnormality of Optic Papilla is Detected:

A tomogram of an area of 6 mm×6 mm near the optic papilla is acquired with a size of 1024×512×16 by circular scanning.

When Nerve Fiber Layer Deficit is Detected:

Since the thickness of the nerve fiber layer needs to be quantified, a tomogram of a rectangular area including a deficit region is acquired with a size of 512×512×128 by raster scanning so as to accurately measure the thickness on a B-scan image.

When Retinal Vascular Lesion is Detected:

Since there is a possibility that the detected lesion may be a macular edema, a tomogram of an area of 6 mm×6 mm near a macula 501c is acquired with a size of 256×256×256 by raster scanning so as to sufficiently include a macula portion having a diameter of about 2 mm.

When Other Lesions such as Soft Drusen are Detected:

Since age-related macular degeneration is suspected, a tomogram of an area of 6 mm×6 mm near the macula 501c is obtained with a size of 512×512×128 by raster scanning so as to detect fine irregularity on the retinal pigment epithelium on a B-scan image.

If a plurality of lesion candidates are detected in step S302, an imaging region is determined for each lesion candidate, and imaging parameters are determined for each lesion candidate. If, for example, the geometric abnormality of an optic papilla and a nerve fiber layer deficit near a macula portion are detected, parameters designating imaging of each of the optic papilla portion and the macula portion are set.

Step S305

In step S305, the tomogram acquisition unit 203 acquires a tomogram from the tomographic imaging apparatus 3 based on the tomographic imaging parameters determined in steps S303 and S304. That is, if a parameter designating the necessity/unnecessity of the acquisition of a tomogram indicates necessity, the tomogram acquisition unit 203 transmits a tomographic imaging request to the tomographic imaging apparatus 3, together with parameters designating the contents of imaging. The tomogram acquisition unit 203 then acquires a tomogram transmitted from the tomographic imaging apparatus 3. The tomogram acquired by the tomogram acquisition unit 203 is transmitted to the tomogram analysis unit 207, display unit 204, and data saving unit 208. If imaging associated with a plurality of regions is designated in step S304, imaging requests using the respective imaging parameters are transmitted to the tomographic imaging apparatus 3 to execute imaging a plurality of number of times.

Step S306

In step S306, the tomogram analysis unit 207 analyzes the tomogram acquired in step S305, and performs image measurement associated with the tomogram or lesion candidate detection from the tomogram. The tomogram analysis unit 207 then transmits the analysis result to the display unit 204 and the data saving unit 208.

When, for example, a tomogram of a macula portion is obtained, a retinal layer thickness is measured by detecting the boundary of the retinal layer using known threshold processing or the like. When a tomogram of the optic papilla is obtained, a cup/disc ratio is obtained by detecting an internal limiting membrane using known threshold processing. The region to be measured is not limited to a retinal layer boundary. For example, a blood vessel may be measured.

In addition, the tomogram analysis unit 207 detects a lesion candidate by comparing an analysis result concerning an eye portion such as a retinal layer thickness with the normal value of an eye portion shape stored in advance and detecting the geometric abnormality of the eye portion when the result falls outside the normal value range. Note, however, that the method of acquiring lesion candidates from a tomogram is not limited to this. For example, it is possible to directly detect a lesion candidate by using density information or morphological information about a tomogram.

Furthermore, it is possible to form a graph or map, e.g., the distribution state of retinal layer thicknesses, for helping the understanding of an image measurement result or lesion candidate detection result.

Note that if a tomogram concerning a plurality of regions is acquired in step S305, the tomogram analysis unit 207 executes processing for each region. If no tomogram is acquired in step S305, the tomogram analysis unit 207 does not execute the processing in step S306.

Step S307

In step S307, the display unit 204 performs the following processing if a tomogram is acquired. That is, the display unit 204 displays, on the monitor 105, the tomogram obtained in step S305 and the tomogram analysis result obtained in step S306 (image measurement or lesion candidate detection result). In this case, for the purpose of, for example, checking an imaging region, it is possible to display together a wide-area image and lesion candidates detected on the wide-area image or a tomogram acquisition range on the wide-area image. Alternatively, it is possible to simultaneously display tomographic imaging parameters. If no tomogram is acquired, it is possible to display, for example, a reason why it is unnecessary to acquire a wide-area image or tomogram.

Figure 7:
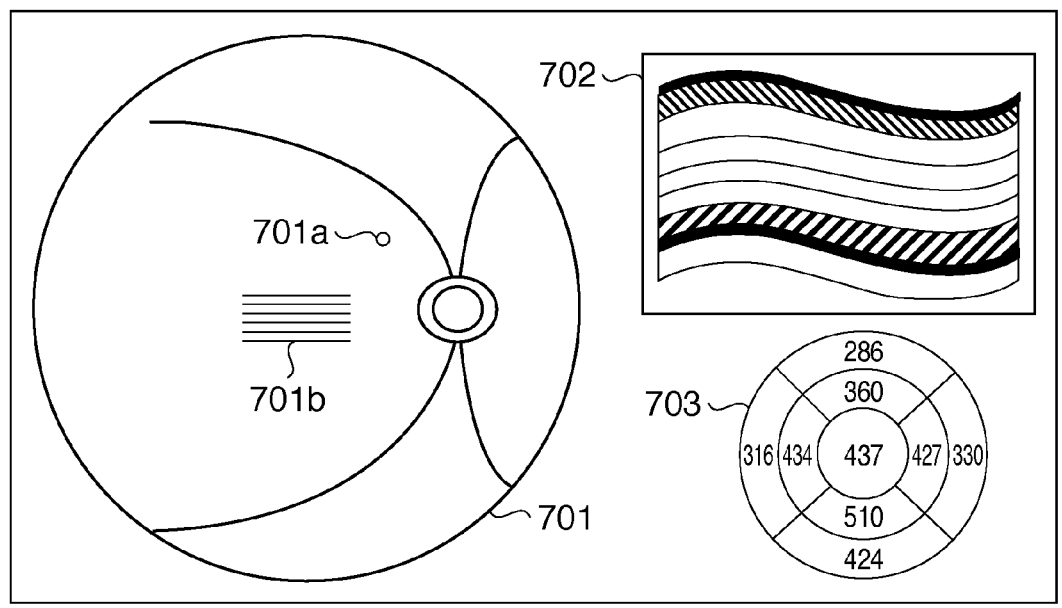
FIG. 7 is a view showing an example of display by the diagnosis support apparatus.

FIG. 7 shows a display example of the lesion candidate detection result obtained by the lesion candidate detection unit 201 and the image measurement result obtained by the tomogram analysis unit 207. In this example, a wide-area image 701, a lesion candidate 701a, and a tomogram acquisition range 701b are displayed on the left side, and an acquired tomogram 702 and a retinal layer thickness map 703 as a tomogram analysis result are displayed on the upper right and the lower right, respectively.

In this example, since the soft drusen 701a is detected on the wide-area image 701, the macula portion 701b is designated as an imaging region, a retinal layer boundary (the thick line portion of 702) is detected from the obtained tomogram 702, and the obtained retinal layer thickness map 703 is displayed.

Step S308

In step S308, the data saving unit 208 saves various kinds of information input in the above steps in association with each other as data of a given patient in the magnetic disk 102. More specifically, the data saving unit 208 saves the wide-area image obtained in step S301, the lesion candidate information obtained in step S302, the tomographic imaging parameters obtained in steps S303 and S304, the tomogram obtained in step S305, and the image measurement or lesion candidate detection result obtained in step S306. Obviously, the data saving unit 208 need not save all these data.

Note that it is possible to save tomographic imaging parameters only when the tomogram acquisition unit 203 cannot acquire any tomogram in step S305 for some reason. Assume, for example, that the tomographic imaging apparatus 3 is not connected to the diagnosis support apparatus 1. In this case, associating wide-area images with tomographic imaging parameters in advance can (manually) obtain a necessary tomogram of a patient afterward. In this case, tomographic imaging parameters can be saved in the header area of a wide-area image file.

Note that data may be saved in an external server (not shown). In this case, the data saving unit 208 transmits these data to the external server.

As described above, this embodiment automatically sets information indicating the necessity/unnecessity of the acquisition of a tomogram and an acquisition range from an analysis result on a wide-area image of an eye portion. This makes it possible to efficiently acquire a tomogram of an eye portion.

In addition, this embodiment performs the wide-area image acquisition processing of acquiring a wide-area image of an eye portion, detects lesion candidates on the eye portion by analyzing the acquired wide-area image, and determines parameters associated with the acquisition of a tomogram of the eye portion based on the lesion candidate detection result. The embodiment then performs the tomogram acquisition processing of acquiring a tomogram of the eye portion based on the determined parameters. In this embodiment, since a portion whose tomogram needs to be acquired is automatically detected to acquire a tomogram in this manner, a tomogram of a necessary portion is acquired in an allowed imaging time or analysis processing time. It is, therefore, possible to efficiently acquire a tomogram of an eye portion.

Note that as described above, it is possible to detect at least one of information indicating the presence/absence of a lesion candidate, the type of lesion candidate, a lesion candidate range, and the degree of a lesion candidate by analyzing a wide-area image of an eye portion and determine parameters associated with the acquisition of a tomogram based on the detection result. In this case, a region whose tomogram should be acquired can be properly determined.

It is also possible to determine parameters associated with the acquisition of a tomogram based on at least the type of lesion candidate detected or a lesion candidate range. In this case as well, a region whose tomogram is to be obtained can be properly determined.

In addition, parameters to be determined may include information indicating the necessity/unnecessity of the acquisition of a tomogram. Furthermore, the necessity/unnecessity of the acquisition of a tomogram may be determined based on at least the seriousness of a lesion candidate determined in advance or an occurrence region. In this case, it is possible to properly determine, based on this parameter, whether to acquire a tomogram.

If a parameter includes information indicating that the acquisition of a tomogram is unnecessary, no tomogram is acquired. In this case, it is possible to implement efficient operation without acquiring any unnecessary tomogram.

In addition, parameters to be determined may include information indicating a region whose tomogram should be acquired. Alternatively, parameters to be determined may include information indicating one of the spatial range of a tomogram to be acquired, a resolution, and a scanning method. In this case, it is possible to confirm a region whose tomogram needs to be obtained, based on these parameters.

It is also possible to perform the display control processing of displaying at least an acquired wide-area image or an acquired tomogram on the monitor. In this case, the doctor can perform proper diagnosis while seeing a wide-area image and a tomogram.

It is also possible to save determined parameters in a storage means such as the magnetic disk 102 in association with a wide-area image. In this case, it is possible to take a proper measure such as acquiring a tomogram afterward based on a wide-area image and parameters.

First Modification

The lesion candidate detection unit 201 in this embodiment detects the geometric abnormality of an optic papilla, a nerve fiber layer deficit, the geometric abnormality of a blood vessel such as arteriovenous crossing, and other lesions such as a soft drusen in the processing in step S302. However, the lesion candidates to be detected by the lesion candidate detection unit 201 are not limited to them. For example, as indicated by non-patent reference 3, a leukoma or hemorrhage can be detected by using a known image feature detection technique based on smoothing differentiation processing. It is possible to detect any kind of lesion candidate as long as it can be detected from a wide-area image of an eye portion obtained from the wide-area imaging apparatus 2.

Non-patent reference 3: Yuji Hatanaka et al., "Automated Hemorrhages and Exudates Detection Method in Ocular Fundus Images", IEIC Technical Report, MI2006-131, pp. 181-184, 2007

In addition, information to be detected from a wide-area image need not necessarily be a lesion candidate as long as it is associated with an eye portion which is obtained from the wide-area image. For example, it is possible to measure a retinal shape by processing a wide-area image and measure the degree of dissociation from a standard shape as a numerical value.

Note that when the lesion candidate detection unit 201 detects a lesion candidate different from those in the above embodiment, the tomogram acquisition parameter determination unit 202 needs to determine imaging parameters for the lesion. Assume that a leukoma is to be detected as a lesion candidate. In this case, whenever a leukoma is detected, it is determined that the acquisition of a tomogram is necessary, and the region is determined as a macula portion. Assume also that the degree of dissociation of a retinal shape from a standard shape is to be measured. In this case, if the value is equal to or more than a predetermined threshold, it is determined that the acquisition of a tomogram is necessary, and a macula portion is imaged.

As described above, lesion candidates are not limited to those exemplified in this case, and this arrangement can be applied to arbitrary lesion candidates.

Second Modification

In addition, imaging parameters to be determined are not limited to the above example. Any parameters can be determined as long as it is possible to describe a rule for determining imaging parameters in accordance with the type or position of a detected lesion candidate.

For example, parameters designating the contents of imaging may be only a parameter designating an imaging region corresponding to a detected lesion candidate. In this case, the region determination unit 206 designates a region to be imaged in accordance with the lesion detection result in the processing in step S304. If, for example, the geometric abnormality of an optic papilla is detected, the optic papilla can be designated. If a retinal vascular lesion is detected, a macula portion can be designated. If a soft drusen or the like is detected, a macula portion can also be designated. If a nerve fiber layer deficit is detected, a region (optic papilla/macula portion) including the deficit can be designated. Alternatively, it is possible to determine an imaging mode indicating a combination of several parameters determined in advance as a parameter designating the contents of imaging. If, for example, a retinal vascular lesion is detected, it is possible to designate an imaging mode B for imaging a macula portion with given settings. If a soft drusen or the like is detected, it is possible to designate an imaging mode C for imaging a macula portion with different settings. At this time, the tomogram acquisition apparatus 3 interprets a concrete imaging range, a concrete scanning method, and the like in accordance with a designated region or imaging mode, and obtains a tomogram based on the interpretation.

Furthermore, parameters designating the contents of imaging may be control parameters for controlling the driving mechanism of the tomogram acquisition apparatus 3 (e.g., control parameters for the angle or the like of a galvanometer mirror). In this case, the (eye portion) diagnosis support apparatus 1 directly controls the tomogram acquisition apparatus 3.

Third Modification

This embodiment uses a fundus camera image, an SLO image, or the like as a wide-area image input to the wide-area image acquisition unit 200. However, it is possible to use, as a wide-area image, a two-dimensional image generated by projecting an OCT tomogram obtained by imaging a wide area. In addition, a wide-area image is not limited to a two-dimensional image, and an OCT tomogram obtained by imaging a wide range with a low resolution can be used. An OCT image with a wide imaging range can be directly acquired from the tomographic imaging apparatus 3 whose imaging angular field is set to the maximum. In addition, it is possible to acquire a wide-area image by imaging a plurality of regions of the same eye in advance by using the tomographic imaging apparatus 3 and concatenating the obtained images by image processing.

Figure 8:
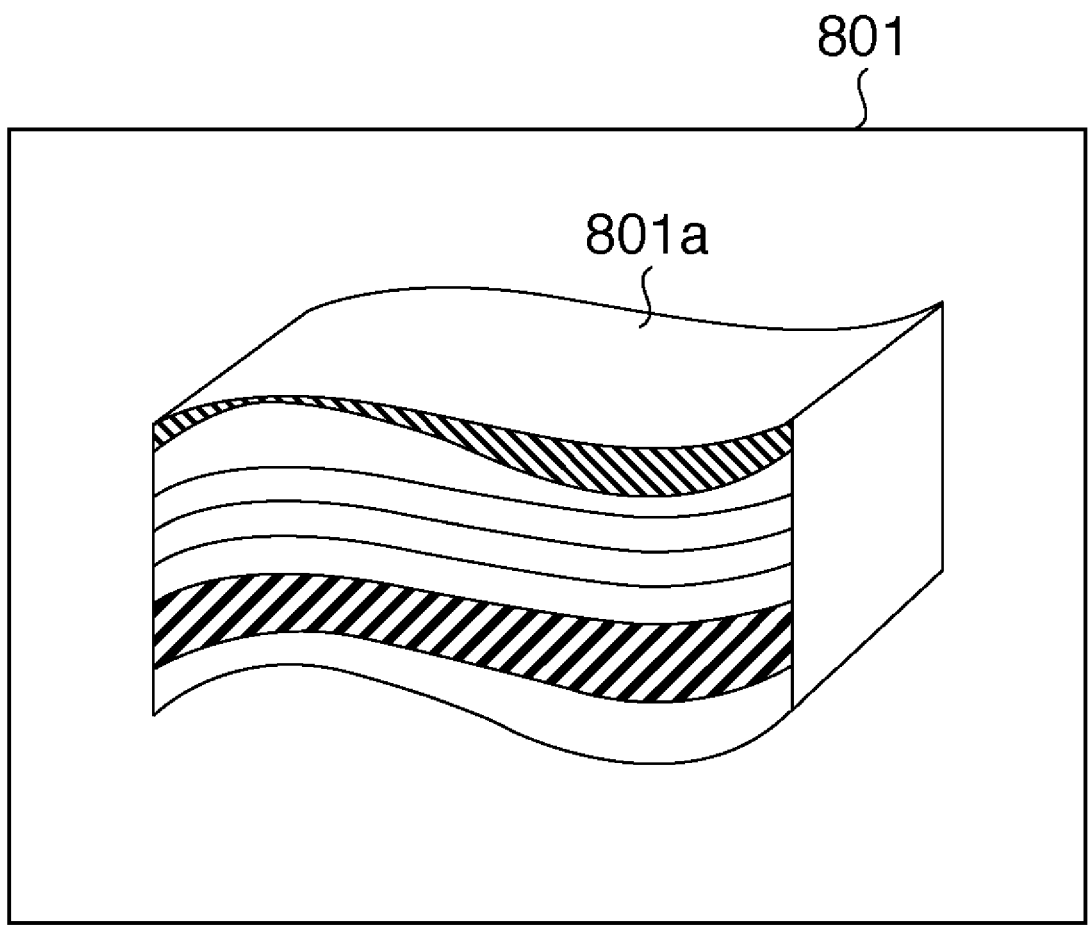
FIG. 8 is a schematic view showing an example of lesion candidates detected by a lesion candidate detection unit.

In this modification, the wide-area image acquisition unit 200 receives an OCT image obtained by imaging a wide area with a low resolution. The lesion candidate detection unit 201 detects a lesion candidate such as nerve fiber layer thickness abnormality by performing processing such as detection of a nerve fiber layer boundary, measurement of a nerve fiber layer thickness, and comparison with a normal nerve fiber layer thickness value. FIG. 8 is a schematic view showing an example of the lesion candidate detected by the lesion candidate detection unit 201. In this case, a region 801*a* smaller in nerve fiber layer thickness than a normal value on a wide-area image 801 is detected as an abnormal portion.

The tomogram acquisition parameter determination unit 202 determines tomographic imaging parameters based on the information associated with the lesion candidate detected by the lesion candidate detection unit 201. The tomogram acquisition unit 203 obtains a local tomogram with a high resolution by using the tomographic imaging parameters. This makes it possible to image and analyze only a necessary region with a high resolution and efficiently acquire a tomogram of an eye portion.

Second Embodiment

Arrangement for Acquiring Wide-Area Image after Imaging/Tomogram from Storage Device The first embodiment has exemplified the arrangement in which the wide-area imaging apparatus 2 and the tomographic imaging apparatus 3 obtain a wide-area image and a tomogram in accordance with imaging requests from the diagnosis support apparatus 1. However, the embodiment of the diagnosis support apparatus is not limited to this. The second embodiment will exemplify a diagnosis support apparatus which acquires, from an external database or storage device, wide-area images and tomograms which have already been obtained and saved, and presents information for supporting diagnosis based on the acquired images.

A diagnosis support apparatus 1 according to the second embodiment is connected to a database 5 (not shown) via a LAN 4. The database 5 stores the medical examination data (wide-area images and tomograms) obtained by imaging by a wide-area imaging apparatus 2 and a tomographic imaging apparatus 3. Note that the diagnosis support apparatus 1 can be configured to read these data from storage devices (not shown) connected to the diagnosis support apparatus 1, for example, various kinds of storage media including an HD, CD-RW drive, and DVD drive.

A flowchart showing a processing sequence in the diagnosis support apparatus 1 according to this embodiment is basically the same as that in the first embodiment. Specific processing contents will therefore be described with reference to FIG. 3. Assume that before the diagnosis support apparatus 1 performs the following processing, a wide-area image (fundus camera image or SLO image) of an eye portion of a patient as a diagnosis target and a tomogram (OCT image) of a wide area of the eye portion are obtained and stored in advance in the database 5.

In step S301, first of all, a wide-area image acquisition unit 200 reads out a wide-area image of an eye portion of a diagnosis target patient stored in the database 5. Note that the image to be acquired in this case includes not only an image as a diagnosis target but also an image of a past case, normal case, typical case, analogous case, or the like.

The processing in steps S302 and S303 is the same as that in the first embodiment.

In step S304, a region determination unit 206 determines acquisition parameters for a local tomogram to be cut out, based on the information concerning the lesion candidate (lesion candidate detection result) detected in step S302. As concrete parameters, a data center position, matrix size, resolution, data arraying method, and the like are determined.

In step S305, the tomogram acquisition unit 203 acquires a local tomogram obtained by cutting out a necessary region from a tomogram of an eye portion of the patient stored in the database 5 by using the tomogram acquisition parameters determined in step S304. Note that the image to be acquired in this case includes not only an image as a diagnosis target but also an image of a past case, normal case, typical case, analogous case, or the like.

The processing in steps S306 and S307 is the same as that in the first embodiment.

As described above, the arrangement of this embodiment is configured to determine whether it is necessary to read out a tomogram from an analysis result on a wide-area image of an eye portion and to automatically set a region from which a tomogram is to be read out. This makes it possible to support diagnosis using tomograms. In addition, since readout and analysis processing of tomograms are not performed more than necessary, diagnosis can be performed efficiently.

Other Embodiments

Obviously, the object of the present invention is also implemented by causing a system or apparatus to execute software program codes for implementing the functions of the above embodiments. In this case, the program codes themselves implement the functions of the above embodiments. The program codes are included in the technical scope of the present invention.

The program codes can be stored in, for example, a computer-readable recording medium and supplied to a system or an apparatus. The object of the present invention can also be implemented by causing the computer (or the CPU or MPU) of the system or apparatus to read out and execute the program codes stored in the recording medium. The recording medium storing the program codes is also included in the technical scope of the present invention As a recording medium for supplying the program codes, a flexible disk, hard disk, optical disk, magnetooptical disk, CD-ROM, CD-R, magnetic tape, nonvolatile memory card, ROM, DVD, or the like can be used.

Note that the program codes are not limited to those having all elements by which the computer implements the functions of the above embodiments by reading out and executing the program codes. That is, the program codes include program codes which achieve the object by operating in cooperation with at least the software or hardware incorporated in the computer.

For example, when an OS or the like running on the computer performs part or all of actual processing on the basis of the instructions of the program codes, and the functions of the above embodiments are implemented by the processing, the program codes are also included in the technical scope of the present invention. Note that OS is an abbreviation for Operating System.

In some cases, for example, the CPU of a function expansion board or function expansion unit inserted in or connected to a computer performs part or all of actual processing on the basis of the instructions of the program codes, and the functions of the above embodiments are implemented by the processing. In such a case, the program codes are also included in the technical scope of the present invention. Note that the function expansion board or function expansion unit can perform such processing by loading the program codes into the memory which it has, and executing them.

Note that the description of the above embodiments is an example of the preferred diagnosis support apparatus of the present invention. The present invention is not limited to this.

The present invention is not limited to the above embodiments and various changes and modifications can be made within the spirit and scope of the present invention. Therefore, to apprise the public of the scope of the present invention, the following claims are made.

The invention claimed is:

1. A fundus image acquiring apparatus comprising:
a fundus image acquisition unit adapted to acquire a fundus image of an eye portion;
a detection unit adapted to detect a location of an optic papilla of a fundus of the eye portion from the fundus image;
a tomogram acquisition unit adapted to acquire, based on the location, a tomogram of the fundus in an area located around the optic papilla by scanning a measurement light in a circle in the area located around the optic papilla; and
a display control unit adapted to cause a display unit to display the fundus image and the tomogram, to cause the display unit to display as parameters the scan used to acquire the tomogram and a resolution of the scan, and to cause the display unit to display a display indicating a location corresponding to the acquired location of the tomogram on the fundus image which is displayed on the display unit.

2. An ophthalmic apparatus comprising:
a detection unit adapted to detect information regarding an optic papilla of a fundus of an eye portion from a fundus image of the eye portion; and
a tomogram acquisition unit adapted to acquire, based on the information, a tomogram of the fundus in an area located around the optic papilla by scanning a measurement light; and
a display control unit adapted to cause a display unit to display the fundus image and the tomogram, to cause the display unit to display as parameters the scan used to acquire the tomogram and a resolution of the scan, and to cause the display unit to display a display indicating a location corresponding to the acquired location of the tomogram on the fundus image which is displayed on the display unit.

3. The ophthalmic apparatus according to claim 2, wherein the tomogram acquisition unit acquires the tomogram by scanning a measurement light in a circle in the area located around the optic papilla.

4. The ophthalmic apparatus according to claim 2 wherein
the detection unit detects a location of the optic papilla from the fundus image; and
the tomogram acquisition unit acquires, based on the location, a tomogram of the fundus in the area located around the optic papilla.

5. An ophthalmic system comprising:
a fundus camera adapted to acquire a fundus image of an eye portion;
a detection unit adapted to detect a location of an optic papilla of a fundus of the eye portion from the fundus image; and
an optical coherence tomography (OCT) apparatus adapted to acquire, based on the location, a tomogram of the fundus in an area located around the optic papilla by scanning a measurement light in a circle in the area located around the optic papilla; and
a display control unit adapted to cause a display unit to display the fundus image and the tomogram, to cause the display unit to display as parameters the scan used to acquire the tomogram and a resolution of the scan, and to cause the display unit to display a display indicating a location corresponding to the acquired location of the tomogram on the fundus image which is displayed on the display unit.

6. An ophthalmic system comprising:
a detection unit adapted to detect information regarding an optic papilla of a fundus of an eye portion from a fundus image of the eye portion; and
a tomogram acquisition unit adapted to acquire, based on the information, a tomogram of the fundus in an area located around the optic papilla by scanning a measurement light; and
a display control unit adapted to cause a display unit to display the fundus image and the tomogram, to cause the display unit to display as parameters the scan used to acquire the tomogram and a resolution of the scan, and to cause the display unit to display a display indicating a location corresponding to the acquired location of the tomogram on the fundus image which is displayed on the display unit.

7. The ophthalmic system according to claim 6, wherein the tomogram acquisition unit acquires the tomogram by scanning a measurement light in a circle in the area located around the optic papilla.

8. The ophthalmic system according to claim 6, wherein
the detection unit detects a location of the optic papilla from the fundus image; and
the tomogram acquisition unit acquires, based on the location, a tomogram of the fundus in the area located around the optic papilla.

9. The ophthalmic system according to claim 6, further comprising a fundus camera adapted to acquire the fundus image, wherein the tomogram acquisition unit is an optical coherence tomography (OCT) apparatus.

10. The ophthalmic system according to claim 6, further comprising a scanning laser ophthalmoscope (SLO) apparatus;
wherein the tomogram acquisition unit is an optical coherence tomography (OCT) apparatus.

11. A tomogram acquisition method comprising:
a fundus image acquisition step of acquiring a fundus image of an eye portion;
a detection step of detecting a location of an optic papilla of a fundus of an eye portion from the fundus image;
a tomogram acquisition step of acquiring, based on the location, a tomogram of the fundus in an area located around the optic papilla by scanning a measurement light in a circle in the area located around the optic papilla; and a display control step of causing a display unit to display the fundus image and the tomogram, causing the display unit to display as parameters the scan used to acquire the tomogram and a resolution of the scan, and causing the display unit to display a display indicating a location corresponding to the acquired location of the tomogram on the fundus image which is displayed on the display unit.

12. An ophthalmic processing apparatus comprising:
a detection unit adapted to detect a location of an optic papilla of a fundus of an eye portion from a fundus image of the eye portion;
a control unit adapted to control an optical coherence tomography (OCT) apparatus to acquire a tomogram of the fundus in an area located around the optic papilla by scanning a measurement light in a circle in the area located around the optic papilla based on the location; and
a display control unit adapted to cause a display unit to display the fundus image and the tomogram, to cause the display unit to display as parameters the scan used to acquire the tomogram and a resolution of the scan, and to cause the display unit to display a display indicating a location corresponding to the acquired location of the tomogram on the fundus image which is displayed on the display unit.

* * * * *